United States Patent
Krasner

(10) Patent No.: US 8,177,554 B2
(45) Date of Patent: May 15, 2012

(54) DEVICE AND METHOD FOR LOCATING A PULP CHAMBER IN A TOOTH

(76) Inventor: Paul R. Krasner, Wayne, PA (US)

( * ) Notice: Subject to any disclaimer, the term of this patent is extended or adjusted under 35 U.S.C. 154(b) by 215 days.

(21) Appl. No.: 12/476,598

(22) Filed: Jun. 2, 2009

(65) Prior Publication Data

US 2010/0304326 A1 Dec. 2, 2010

(51) Int. Cl.
*A61C 3/00* (2006.01)
(52) U.S. Cl. ............................. 433/75; 433/72
(58) Field of Classification Search ............... 433/72, 433/75, 139, 73, 74, 76, 177, 178; 408/104, 408/105, 106, 107, 108, 109, 110, 111, 112, 408/115 B
See application file for complete search history.

(56) References Cited

U.S. PATENT DOCUMENTS

| | | | | |
|---|---|---|---|---|
| 472,004 | A * | 3/1892 | Sweet et al. | 433/75 |
| 1,502,970 | A * | 7/1924 | Van Houten | 433/170 |
| 2,628,512 | A * | 2/1953 | Lankford | 408/79 |
| 3,156,049 | A * | 11/1964 | Zolnowski | 33/513 |
| 3,436,826 | A * | 4/1969 | Edelman | 433/75 |
| 4,007,530 | A * | 2/1977 | Gaccione | 433/139 |
| 4,117,596 | A * | 10/1978 | Wallshein | 433/9 |
| 4,639,221 | A * | 1/1987 | Sairenji | 433/139 |
| 4,661,063 | A * | 4/1987 | Levy | 433/139 |
| 5,503,556 | A * | 4/1996 | Leonard et al. | 433/139 |
| 5,888,065 | A * | 3/1999 | Sussman | 433/76 |
| 6,390,814 | B1 * | 5/2002 | Gardiner | 433/75 |
| 6,425,875 | B1 | 7/2002 | Reifman | |
| 6,520,775 | B2 | 2/2003 | Lee | |
| 6,609,911 | B2 * | 8/2003 | Garrison | 433/139 |
| 6,869,283 | B2 * | 3/2005 | Sussman | 433/76 |
| 6,968,229 | B2 | 11/2005 | Siemons | |
| 7,121,827 | B2 | 10/2006 | Lampert | |
| 7,172,421 | B2 * | 2/2007 | Bina et al. | 433/165 |
| 7,905,726 | B2 * | 3/2011 | Stumpel | 433/75 |
| 2005/0177074 | A1 | 8/2005 | Becker | |
| 2006/0240378 | A1 * | 10/2006 | Weinstein et al. | 433/76 |
| 2010/0092912 | A1 * | 4/2010 | Machado et al. | 433/76 |
| 2010/0203479 | A1 * | 8/2010 | Bulloch et al. | 433/215 |
| 2010/0311006 | A1 * | 12/2010 | Lancieux et al. | 433/75 |

OTHER PUBLICATIONS

Krasner et al, "Anatomy of the Pulp-Chamber Floor", Journal of Endodontics, vol. 30, No. 1, Jan. 2004, pp. 5-16.

* cited by examiner

*Primary Examiner* — John P Leubecker
*Assistant Examiner* — Christopher Sponheimer
(74) *Attorney, Agent, or Firm* — William H. Eilberg

(57) ABSTRACT

A pulp chamber locator assists a dentist in performing a root canal procedure. The device includes a generally circular plate and a plurality of struts extending from the plate. The plate has a hole in the vicinity of its center. The device is inserted over a tooth, such that the struts engage the cemento-enamel junction of the tooth. The hole then indicates the proper point of entry for a dental instrument. The device may also include a rotatable indicator for showing the proper angle of entry, to insure that the instrument reaches the pulp chamber of the tooth. The dentist adjusts the position of the indicator, based on information provided by an X-ray or equivalent, and positions the dental instrument so as to be generally parallel with the indicator.

4 Claims, 11 Drawing Sheets

DEVICE AND METHOD FOR LOCATING A PULP CHAMBER IN A TOOTH

BACKGROUND OF THE INVENTION

The present invention relates to the field of dentistry, and provides a device and method useful in performing a root canal procedure. Specifically, the invention enables a dentist to find the proper entry point, and entry angle, to access the pulp chamber of a tooth.

Root canal treatment is performed in response to an infection of the pulp of the tooth. The pulp is found in an internal chamber, which is beneath the crown and not visible from the outside. When the pulp becomes damaged, either due to tooth decay, or to dental restoration procedures or trauma, the pulp can become severely inflamed and then infected. This degeneration will often result in a severe toothache and/or a movement of the infection into the bone near the tooth roots. Therefore, when the pulp becomes damaged, it must be removed. This is done through the process of a root canal procedure.

As shown in FIG. 1, the pulp of the tooth fills a contiguous space which includes root canals 2, adjacent to the tooth roots 4, and which also includes a pulp chamber 3, located beneath the crown 1 of the tooth. In a root canal treatment, the pulp must be removed in its entirety, including both the pulp in the pulp chamber, near the crown, as well as the pulp in the root canals.

In a root canal procedure, the tooth is first penetrated so as to expose the coronal portion of the pulp (i.e. the pulp near the crown of the tooth). All of the pulp is then removed, and the empty pulp chamber and root canals are sterilized with various medicaments to insure removal of most bacteria. Finally, the root canals are hermetically filled with a non-toxic filler.

The tooth anatomy shown in FIG. 1, and in many of the other figures, is idealized. In the figure, the crown is well-formed, and the pulp chamber is clearly located directly beneath the crown. But in a real clinical setting, the location of the pulp chamber is often very difficult to ascertain. This difficulty can be due to a variety of reasons:

1) The crown of the tooth may be very heavily restored with old amalgams, composite fillings, or gold inlays.

2) The tooth may have an artificial crown that hides the underlying normal tooth structure. Thus, the normal anatomy of an unrestored tooth, or a lightly restored tooth, which is usually used as guidance for initial penetration, is gone. The artificial crown may be incorrect anatomically, and may give no indication of the true occlusal anatomy of the tooth which is normally used as a guide for initial penetration.

3) The tooth may be tilted or rotated in any direction. When this happens, a crown may be constructed in such a position to correct the tilting discrepancy. This tilting is likely to confuse the dentist with regard to the proper penetration angle for a dental burr.

4) In an elderly patient, the walls of the pulp chamber and root canals narrow, and the pulp chamber may not be easily seen or observed.

5) Almost all dentists currently perform root canal treatments with the patient lying back in a prone position. When the patient is lying back, the angle of the tooth is further distorted, and the correct penetration point and angle of penetration becomes difficult to ascertain.

6) In practice, in many teeth, the pulp chamber may be very small, thready, and calcified, and very different from the idealized concept illustrated in the drawings. The dentist must often penetrate into areas that could be as small as 1 mm in diameter. The margin for error is therefore very, very small.

All of the above conditions, as well other clinical factors, such as inexperience, may lead to difficulty in finding the pulp chamber. An error in locating the pulp chamber can have severe consequences.

First, failure to locate the pulp chamber may prevent the pulp from being removed, and therefore the patient's pain cannot be relieved, and the procedure cannot be performed.

Secondly, if the exact position of the pulp chamber is not known, the penetrating burr may deviate from the proper path needed to enter the pulp chamber. This deviation can cause perforation of the crown, which can lead to loss of the tooth.

Finally, excessive digging around the inside of the tooth can weaken the tooth. It is preferable that the tooth be penetrated not more than once.

Thus, it is imperative that the dentist use every possible aid in locating the pulp chamber. In the prior art, the dentist has been able to rely only on X-rays, on a knowledge of tooth anatomy, and on clinical observations of the patient.

The above methods are ineffectual. The X-ray is only a two-dimensional picture of a three-dimensional object. Knowledge of tooth anatomy is often unhelpful because the structure of the tooth may have dramatically changed due to previous dental work. And clinical observations can be deceptive due to the presence of an artificial crown or other restoration.

A method for locating the pulp chamber has been described in the article entitled "Anatomy of the Pulp-Chamber Floor", by Paul Krasner et al, Journal of Endodontics, Vol. 30, No. 1 (January 2004). The method uses, as a reference point, the cemento-enamel junction (CEJ), which is the junction of the cementum 5 and the enamel 6 of the tooth, as shown in FIG. 1. The CEJ is essentially the "neck" of the tooth. It is where the enamel of the tooth meets the cementum of the roots. In the cited paper, it is shown that if the perimeter of the tooth is known at the CEJ, then the pulp chamber always lies immediately below the center of this perimeter. That is, the pulp chamber of every tooth is centrally located relative to the external perimeter of the tooth, at the CEJ.

However, the cited article does not provide a practical solution to the problem of locating the pulp chamber. A dentist could probe around the neck of a tooth, but still must form a mental image of its perimeter, and then must translate this knowledge to determine the appropriate point of initial penetration on the occlusal surface of the tooth. This process is very difficult because the gingiva at the neck of the tooth is often swollen and inflamed. Moreover, the process of mentally imaging the structure of the tooth is difficult for many dentists.

In summary, dentists currently have surprisingly little practical information about the true relationship between the observed crown of the tooth, and the root upon which it sits.

The present invention solves the above problem, by providing a simple device and method for locating the pulp chamber of a tooth. The invention provides a simple device which can be easily attached to the tooth, and which can directly show the dentist not only where to enter the tooth, but also the proper angle with which to penetrate the tooth.

SUMMARY OF THE INVENTION

The present invention provides a pulp chamber locator, and a method of using the same, for assisting a dentist in performing a root canal procedure.

The pulp chamber locator comprises a generally circular plate having a hole in the vicinity of the center of the plate. A plurality of flexible struts extend from the periphery of the plate. The struts and the plate are sized such that the device can grip the tooth by friction.

In using the device, the dentist inserts the pulp chamber locator onto the tooth, such that the struts engage the tooth at the cemento-enamel junction. When the device is inserted in this way, the hole then identifies the point, on the tooth, at which to begin to drill. The dentist may use a marking tool, inserted through the hole, to mark the proper entry point on the tooth. The device may be removed from the tooth before drilling, or it may be kept in place during the procedure.

In another embodiment, the pulp chamber locator includes a rotatable indicator, attached to the periphery of the plate. The position of the indicator is adjusted by the dentist, in accordance with information obtained from an X-ray or equivalent, to indicate the proper angle of entry into the tooth. It is important that the dental instrument enter the tooth not only at the correct position, and also at the correct angle. The device of the present invention insures that the dental instrument will reach the pulp chamber directly, without causing undue damage to the tooth.

The present invention therefore has the primary object of providing a method and apparatus for locating a pulp chamber of a tooth.

The invention has the further object of reducing the risk of tooth damage during a root canal procedure.

The invention has the further object of assisting a dentist in performing a root canal procedure.

The invention has the further object of providing an apparatus and method which enables a dentist to drill reliably into a tooth, during a root canal procedure, so as to reach the pulp chamber of the tooth with the minimum necessary amount of drilling.

The invention has the further object of providing directional guidance to a dentist, with regard to the location of a pulp chamber of a tooth, and wherein such guidance overcomes deceptive directional indications caused by previous dental work performed on the tooth.

The reader skilled in the art will recognize other objects and advantages of the invention, from a reading of the following brief description of the drawings, the detailed description of the invention, and the appended claims.

DETAILED DESCRIPTION OF THE INVENTION

The device of the present invention enables a dentist easily to locate the pulp chamber of a tooth. Thus, in this specification, the device will be called a pulp chamber locator.

Figure 1:
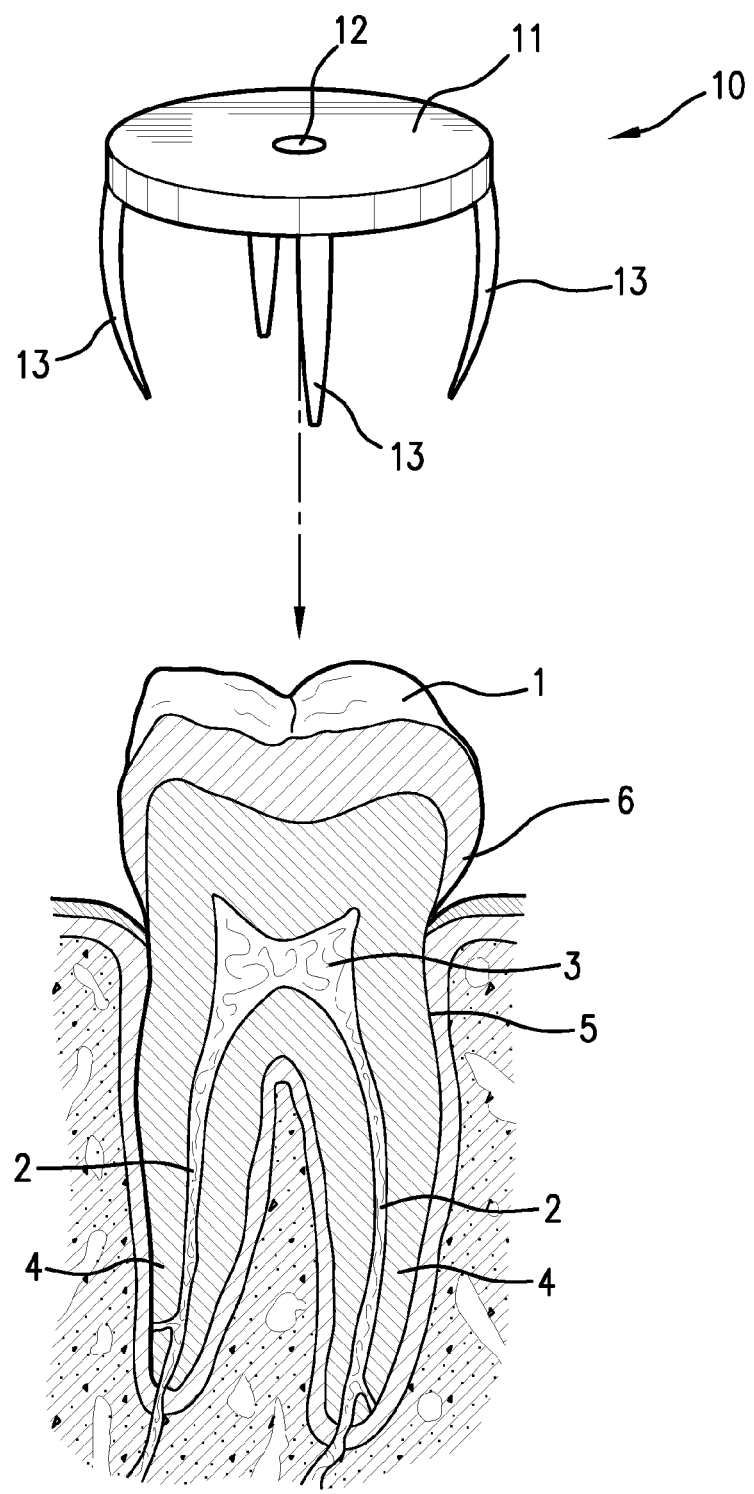
FIG. 1 provides a cross-sectional view of a tooth, and shows, in a perspective view, the pulp chamber locator of the present invention as it is about to be placed over the crown of the tooth.

FIG. 1 shows the pulp chamber locator 10 before it has been attached to the crown 1 of a tooth. The pulp chamber locator comprises a plate 11 which is generally flat and of generally circular shape. In the center of the plate is a hole 12. A plurality of struts 13 are connected to the plate, at the periphery of the plate, and extend downward from the plate. Each strut thus has a first end which is attached to the plate, and a second end which is a free end. In the embodiment shown, there are four struts. In most preferred embodiments, there may be four to six such struts, but the number can be varied.

Preferably, the plate and the struts are made of plastic, but the invention is not limited to a particular choice of material. Preferably the plate and the struts are formed of one piece. The struts are generally perpendicular to the plate.

The struts are flexible and resilient, and therefore can conform to, and grip, a crown of a tooth, with reasonable tightness, for a variety of tooth sizes and shapes. It is preferred that the struts, in their natural (unexpanded) condition, define a volume which is at least slightly smaller than that of the tooth to which the device will be attached. Thus, when the device is inserted over the crown of the tooth, the struts will become elastically deformed, causing the device to be held against the tooth by friction. The struts should have a length which is long enough to reach and grip the cemento-enamel junction (CEJ) of most teeth, but not too long such that the plate is positioned too far above the tooth. The figures show the ideal condition, i.e. the free ends of the struts just reach the CEJ, while the plate sits immediately atop the crown of the tooth.

FIGS. 1-6 illustrate the sequence of steps in the use of the pulp chamber locator of the present invention.

As described above, FIG. 1 shows the pulp chamber locator as it is about to be inserted over the crown of the tooth.

Figure 2:
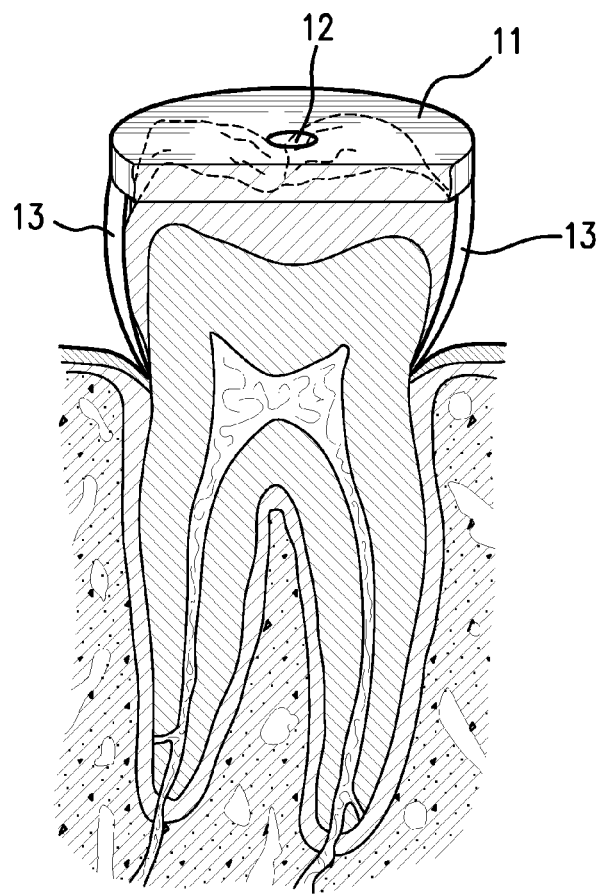
FIG. 2 provides a cross-sectional view of a tooth, and shows, in a broken-away elevational view, the pulp chamber locator of the present invention inserted over the crown.

FIG. 2 shows the pulp chamber locator after it has been inserted over the crown of the tooth. FIG. 2 shows how the struts 13 of the device grip the tooth at the cemento-enamel junction (CEJ), which is the "neck" of the tooth.

Figure 3:
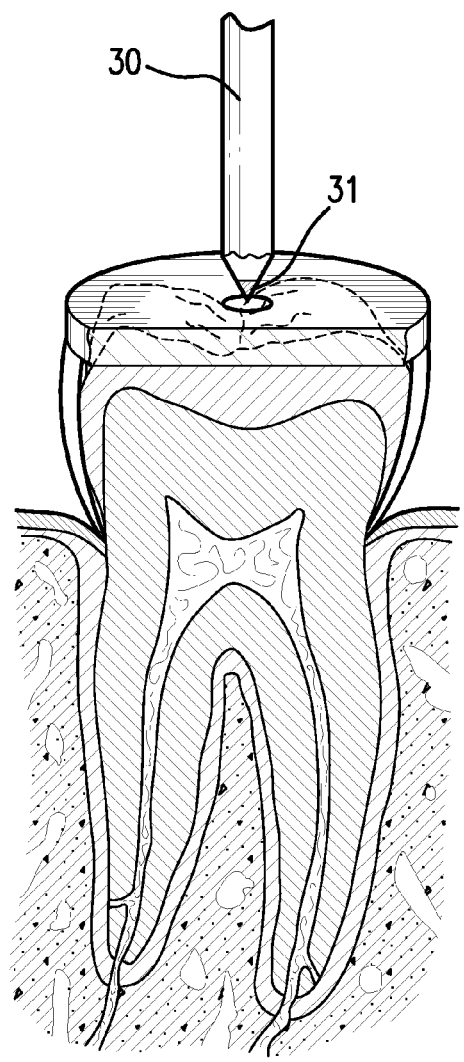
FIG. 3 provides a view similar to that of FIG. 2, also showing a marking tool used to indicate where entry into the tooth shall be made.

FIG. 3 shows the use of marking tool 30 to make a mark at the point, on the crown of the tooth, at which a dental instrument should enter the tooth. The marking tool can be a pen or pencil, or their equivalents, and preferably has a point 31 which is sufficiently thin to pass through the hole 12 in the plate.

Figure 4:
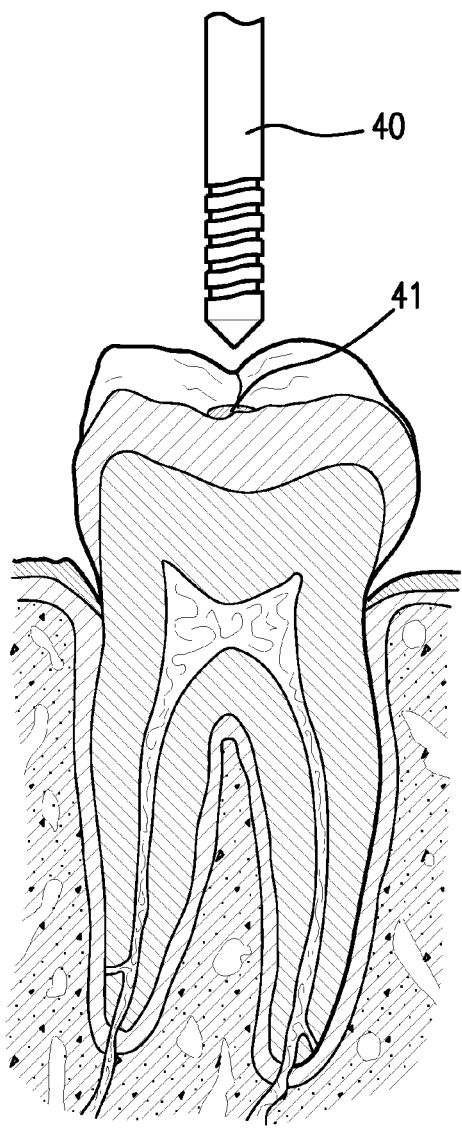
FIG. 4 provides a cross-sectional view of a tooth after it has been marked as shown in FIG. 3, the figure also showing a dental instrument approaching the marked portion of the tooth.

FIG. 4 shows the tooth in which the pulp chamber locator has been removed, and in which the mark 41 remains. The figure shows the approach of a dental instrument 40, which can be a dental burr or drill, or equivalent. The dental instrument is positioned to enter the tooth at the location of the mark 41.

Figure 5:
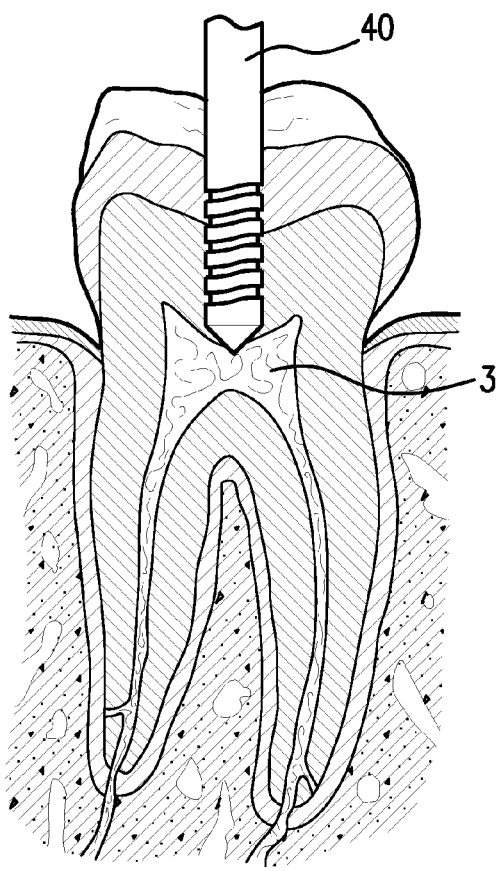
FIG. 5 provides a view similar to FIG. 4, but showing the dental instrument after it has penetrated to the pulp chamber.

FIG. 5 shows the dental instrument 40 after it has penetrated the tooth, and has reached pulp chamber 3.

Figure 6:
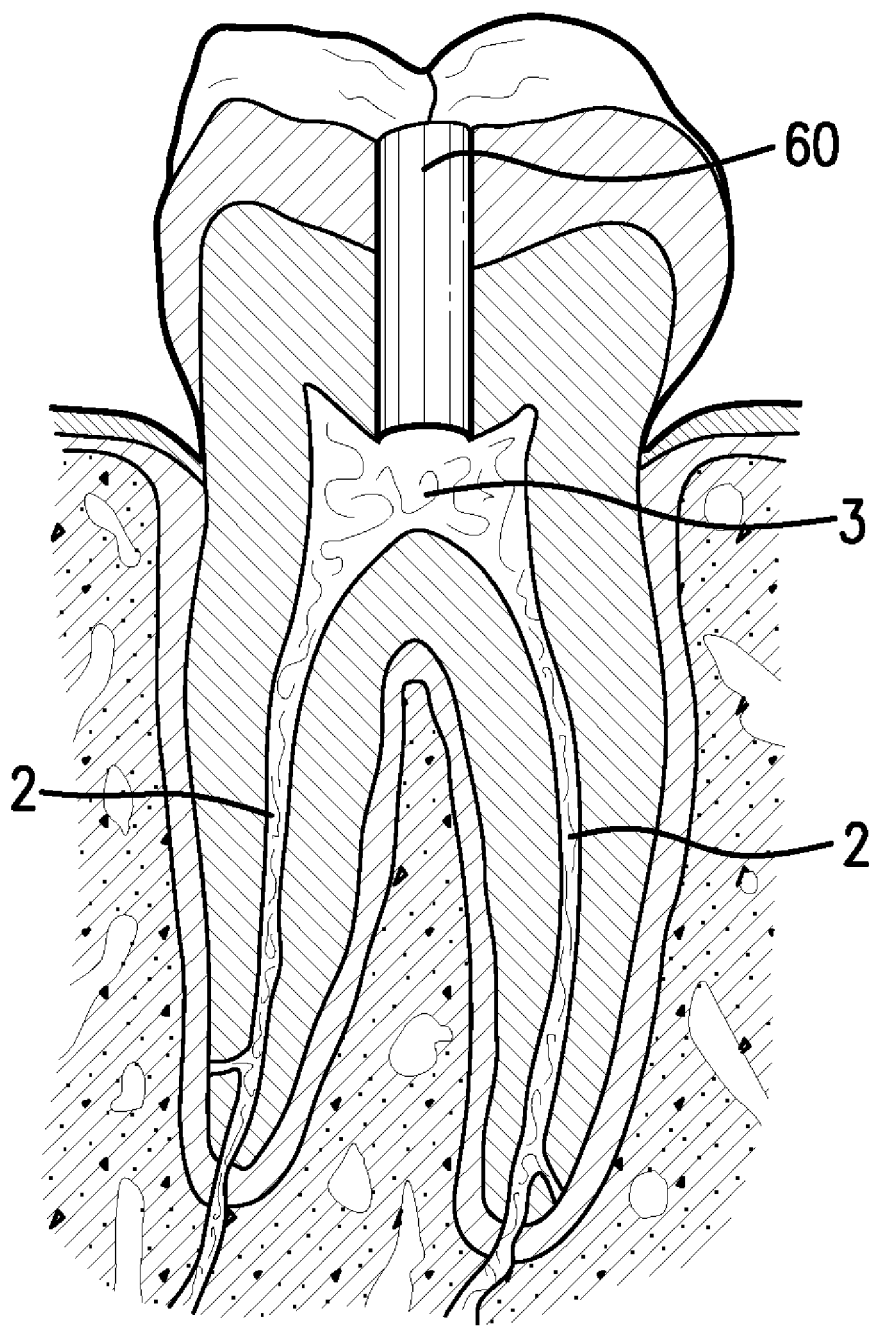
FIG. 6 provides a view similar to that of FIG. 5, but showing an opening or channel formed in the tooth, through which pulp from the pulp chamber can be withdrawn.

FIG. 6 shows the tooth having opening or channel 60 which has been formed by the dental instrument. The pulp in the pulp chamber 3, as well as the pulp in root canals 2, can now be withdrawn from the tooth. The opening or channel also allows medicaments, and, ultimately, fillers, to be injected from the outside, into the pulp chamber and root canals.

Figure 7:
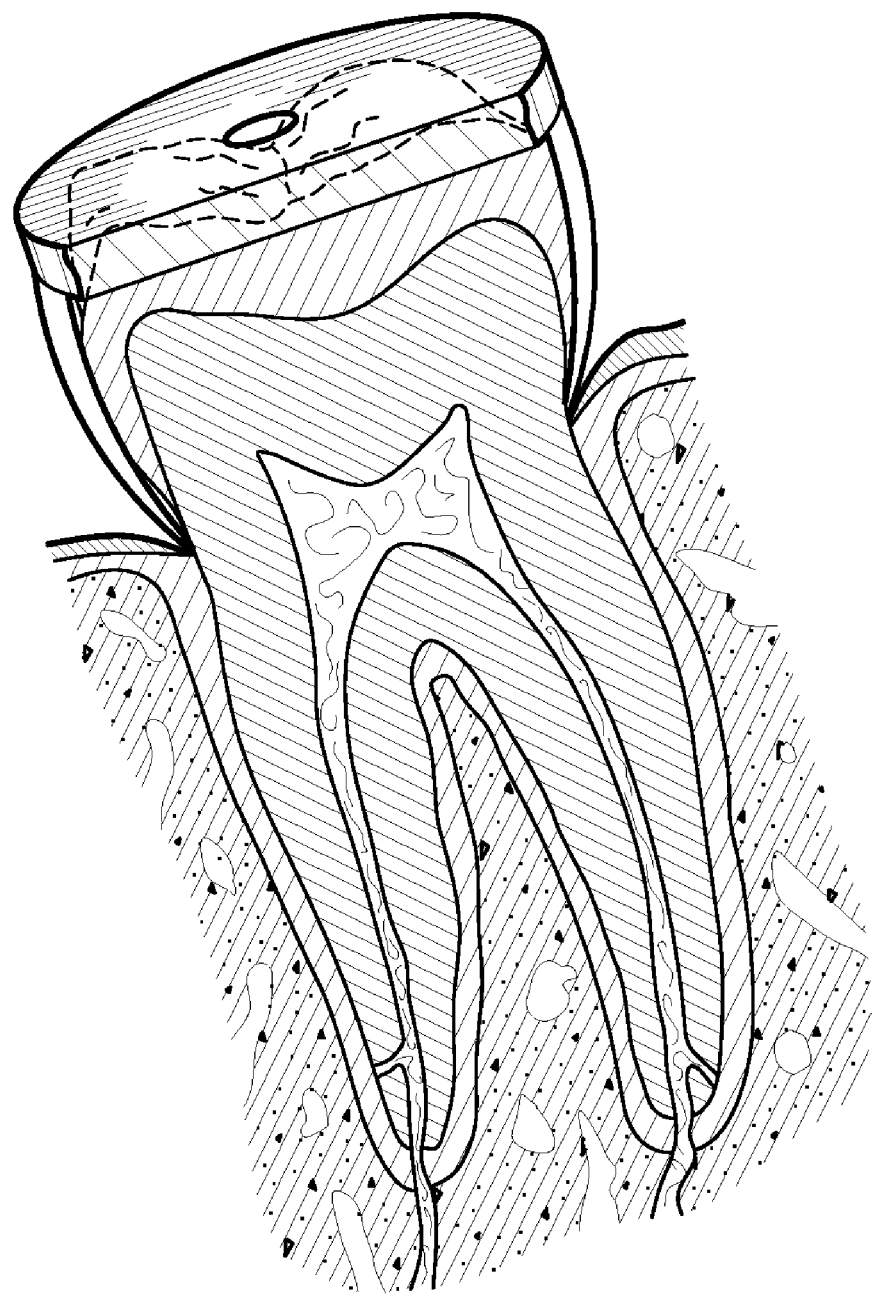
FIG. 7 provides a view which is similar to that of FIG. 2, except that the tooth is crooked, or angled relative to the horizontal.

FIG. 7 illustrates a common situation, in which the tooth is angled relative to the horizontal. The dentist must pay attention to the angle, because, if the dental instrument is inserted, say, perpendicular to the floor, and not parallel to the axis of the tooth, the instrument may miss the pulp chamber entirely.

FIGS. 8-10 and 12-13 show an alternative embodiment of the present invention, in which the pulp chamber locator includes an indicating means for showing the correct entry angle for the dental instrument.

Figure 8:
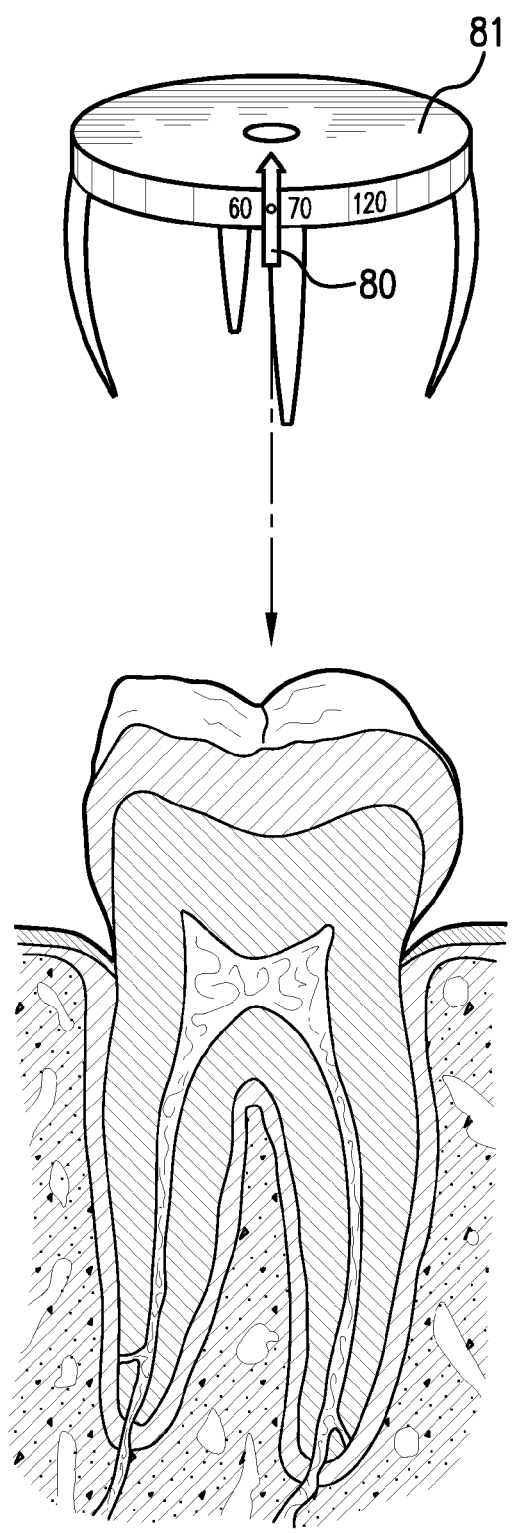
FIG. 8 illustrates an alternative embodiment of the invention, in a view similar to that of FIG. 1, showing a means for indicating the correct entry angle for the dental instrument, the embodiment being suitable for use when the tooth is crooked, as in FIG. 7.
Figure 12:
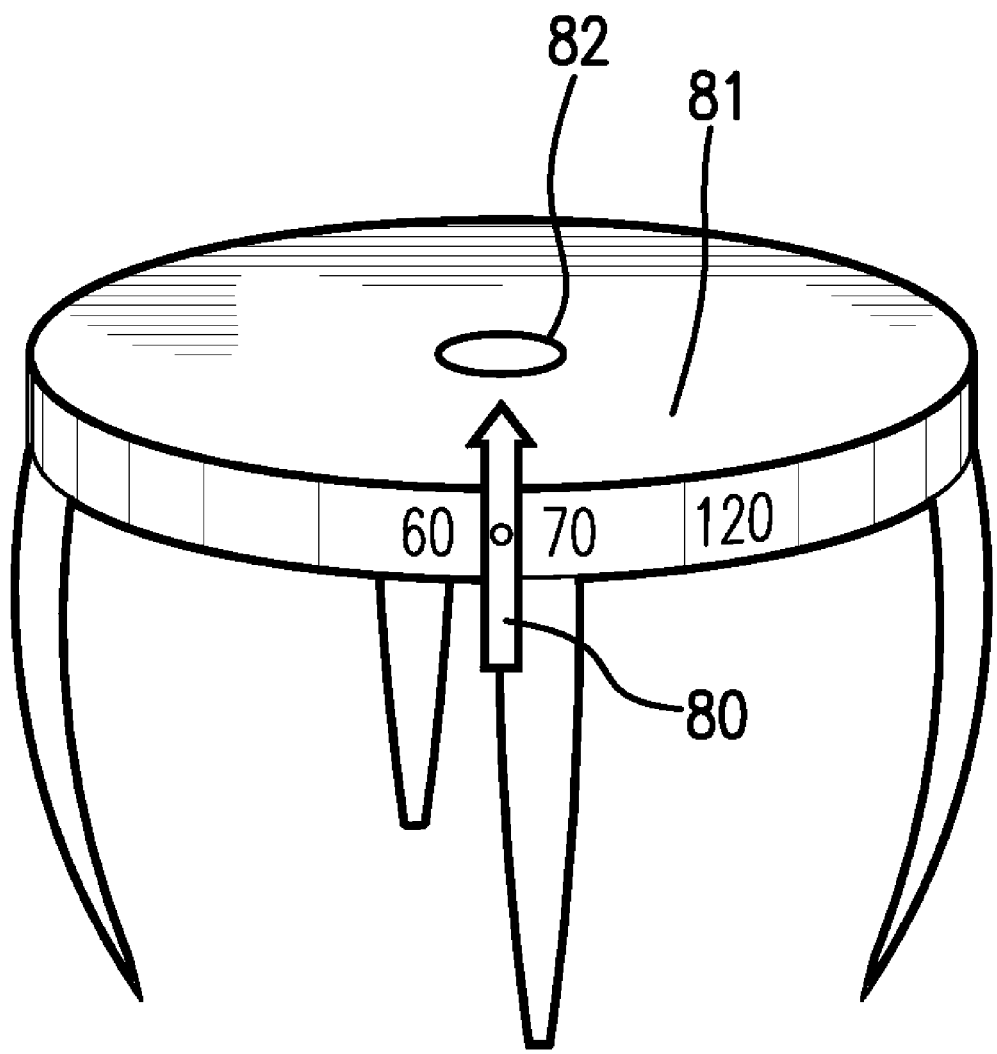
FIG. 12 provides a perspective view of the pulp chamber locator of the present invention, showing the embodiment which includes the angle indicator.

In this alternative embodiment, as particularly shown in FIGS. 8 and 12, the pulp chamber locator includes a rotatable indicator 80, the rotatable indicator being rotatably attached to the periphery of the plate portion 81 of the device. The rotatable indicator is an elongated member defining a pointer or the like. The plate portion is preferably marked with angle indications. When the pulp chamber locator is inserted over the crown of a tooth, the dentist refers to an X-ray, or equivalent, and uses the information from the X-ray to determine the proper angle of entry. The dentist may then adjust the rotatable indicator to signify the desired angle. The operation of the invention is otherwise the same as described with respect to the first embodiment.

Figure 9:
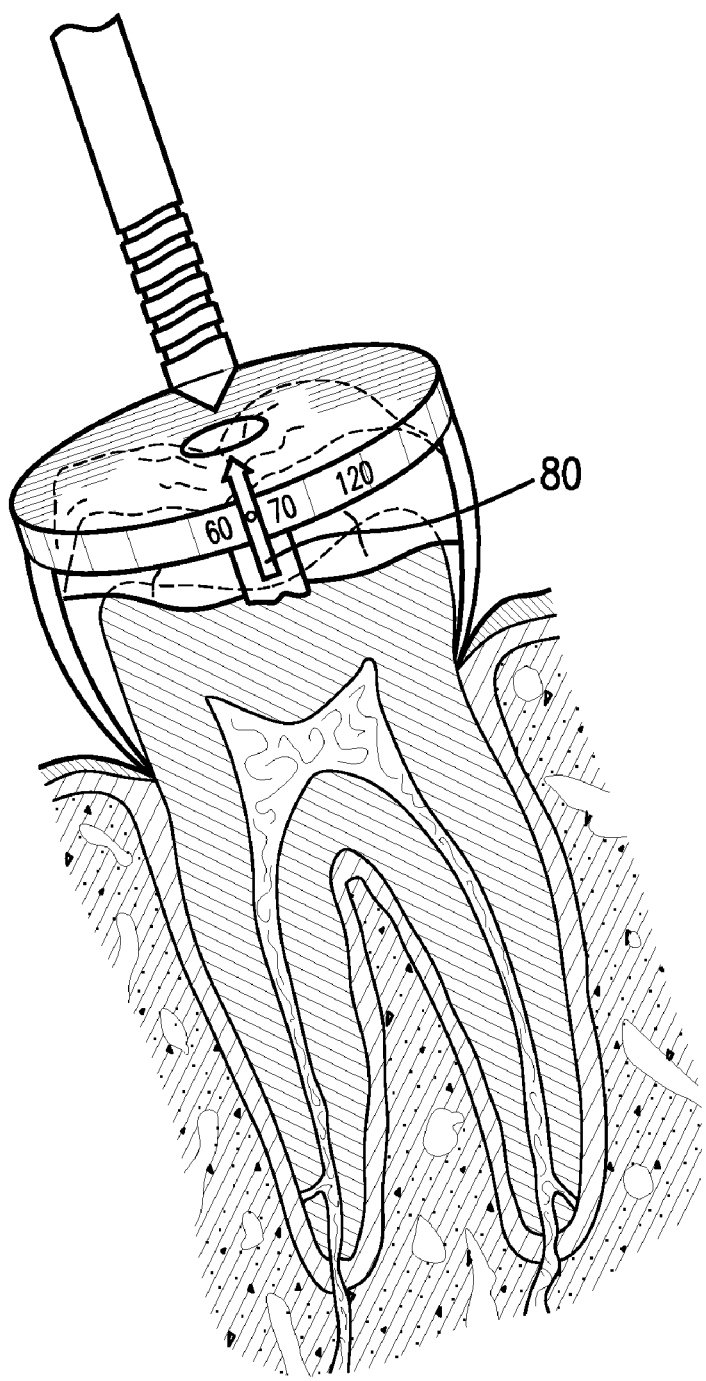
FIG. 9 provides a view similar to that of FIG. 8, in which the angle indicator shows the proper angle of entry for a dental instrument.
Figure 10:
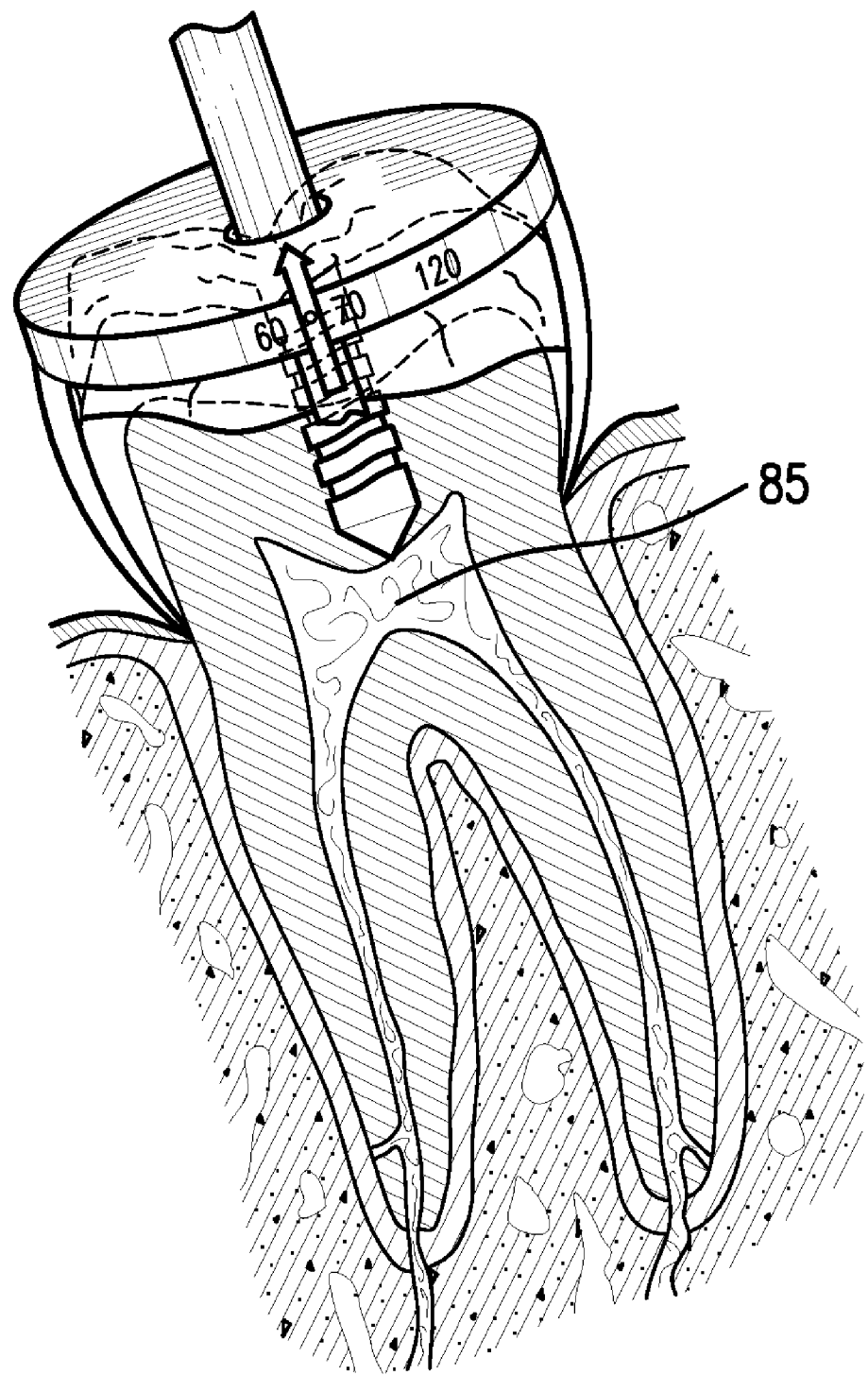
FIG. 10 provides a view similar to that of FIG. 9, in which the dental instrument has penetrated through the hole of the pulp chamber locator, and has reached the pulp chamber.

As seen in the sequence of drawings shown in FIGS. 8-10, the pulp chamber locator is first attached to the tooth, as illustrated in FIG. 8. The rotatable indicator 80 is adjusted according to the information shown in an X-ray, and a dental instrument is applied to the tooth, as shown in FIGS. 9 and 10. Note that the dental instrument passes through the hole in the plate of the pulp chamber locator, and at an angle which is parallel to that of the rotatable indicator. Thus, FIG. 10 shows the dental instrument extending into the tooth both at the correct entry position, and with the correct entry angle, so as to reach the pulp chamber 85.

In an alternative to the above-described procedure, the pulp chamber locator could be removed before penetration of the tooth (as was shown in the first embodiment), in which case the dentist would need to remember the angular indication that was provided when the device was attached.

Note that rotation of the indicator 80, of FIG. 12, has no effect on the position of the hole 82 in the plate 81 of the pulp chamber locator. That is, the proper point of entry is always the same, regardless of the proper angle of entry.

Figure 11:
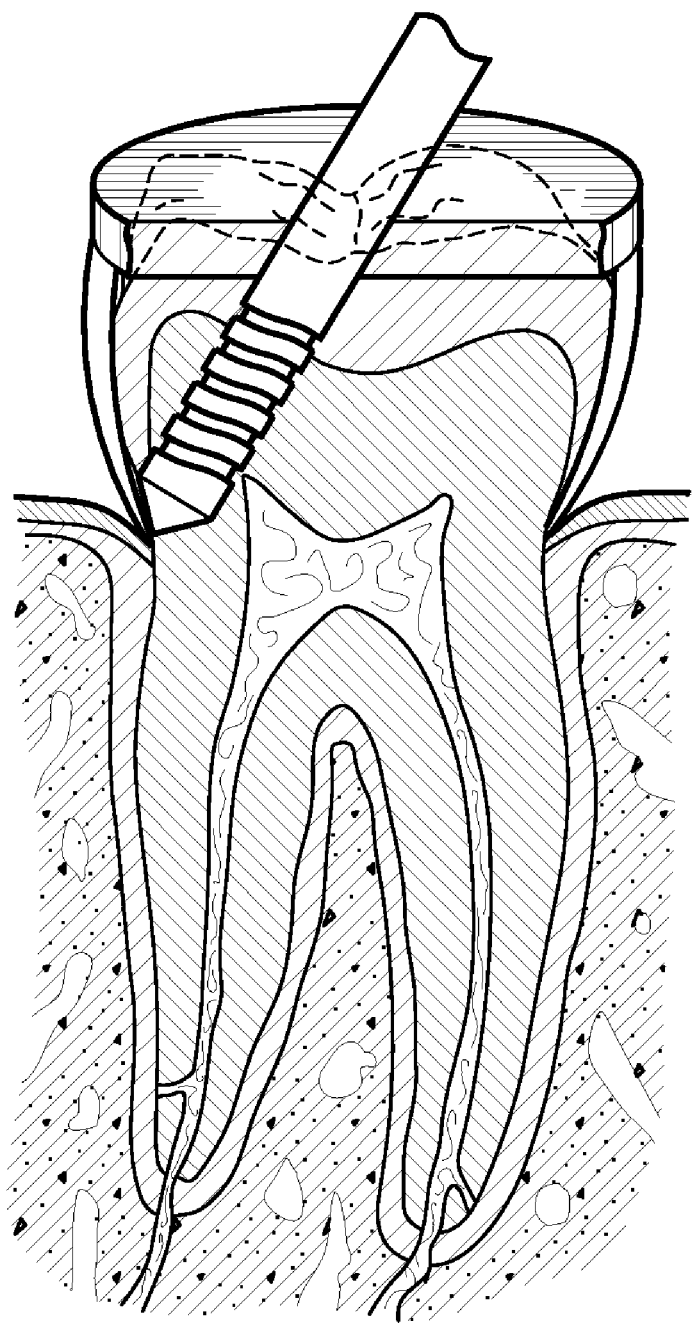
FIG. 11 provides a view similar to those of FIGS. 9 and 10, in which the dental instrument has entered the tooth at the proper location, but in which the angle of entry was not correct.

FIG. 11 illustrates a situation in which the dental instrument has entered the tooth at the correct location, as determined by the position of the hole in the plate portion of the pulp chamber locator, but at an incorrect angle. In the example represented by FIG. 11, the instrument misses the pulp chamber entirely, and will likely cause damage to the tooth.

Figure 13:
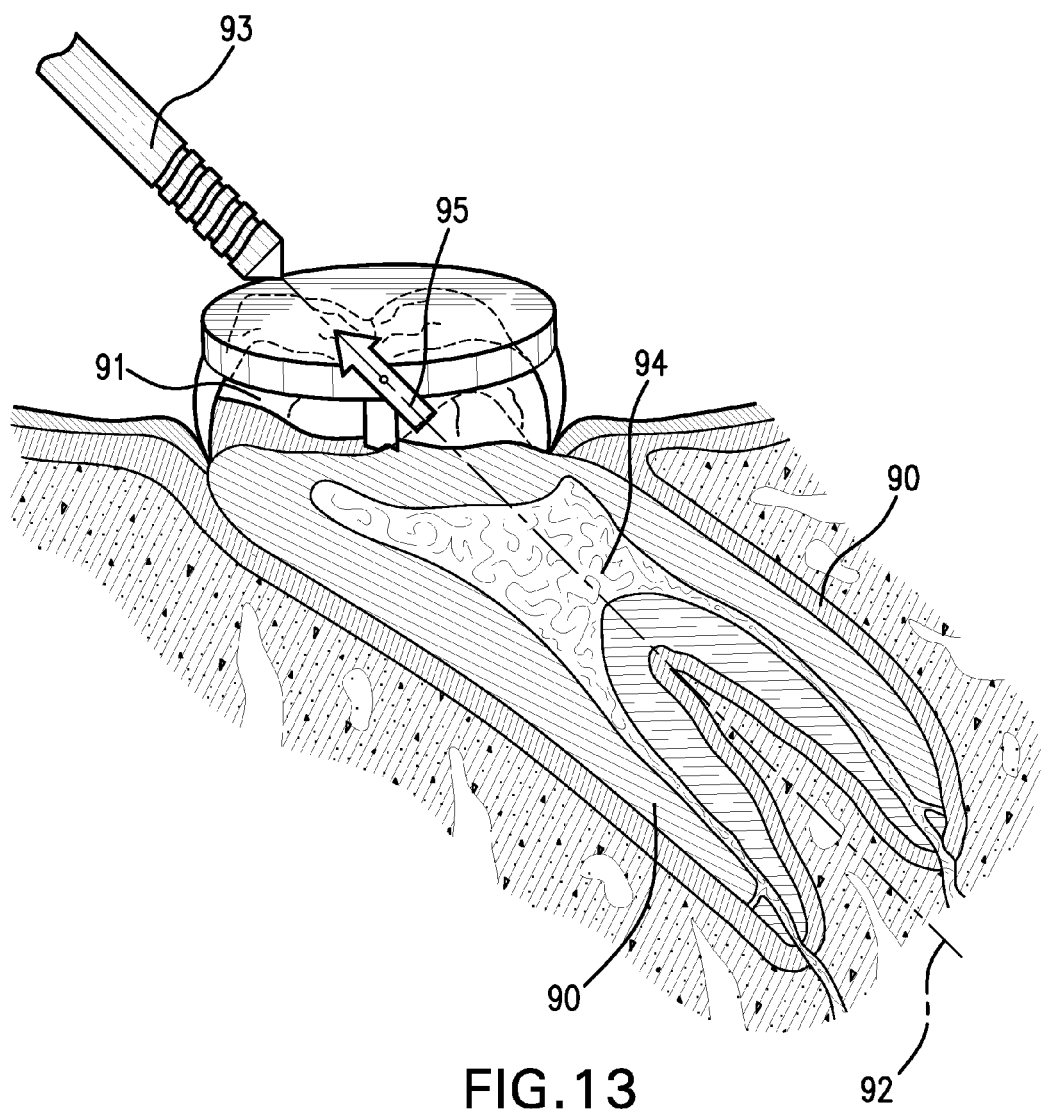
FIG. 13 provides a view similar to that of FIG. 9, but illustrating a case in which the roots of the tooth are greatly angled, and in which the crown of the tooth makes a different angle relative to the horizontal, and in which the angle indicator shows the correct angle for entry of the dental instrument.

The need for the rotatable indicator is especially clear in the situation represented by FIG. 13. In FIG. 13, the tooth roots 90 are clearly angled relative to the horizontal, but the tooth has an artificial crown 91. The crown defines an axis which is vertical relative to the paper, but which is clearly not parallel to the axis 92 of the roots. Thus, if the dental instrument were inserted so as to be parallel to the axis of the artificial crown, the instrument would clearly miss the pulp chamber 94. However, because rotatable indicator 95 shows the correct angle, the instrument 93 can be inserted at the correct angle, i.e. parallel to axis 92. When using the entry angle shown, the instrument will clearly reach the pulp chamber. Note that the indicator 95 is clearly not aligned with the axis of the crown, but it nevertheless indicates the correct angle of entry.

A tooth can have a deceptive form for other reasons. For example, sometimes a patient has had orthodontic treatment, and the tooth may have an unusual inclination. Also, once a rubber dam has been placed on the tooth, all orientation is lost. The rotatable indicator gives the dentist the approximate angle of the tooth. Each tooth is different, so the angle of inclination may be different for each tooth.

In using the embodiment having the rotatable indicator, the dentist first measures the angle of inclination from the X-ray of the patient's teeth, using a protractor. The dentist then sets the rotatable indicator at the measured angle. This is the angle at which to penetrate at the entry point dictated by the pulp chamber locator.

In the preferred embodiment, the rotatable indicator is made of plastic. But the invention is not limited to the use of a particular material.

In the above description, the pulp chamber locator was removed from the tooth before penetration, in the first embodiment, and was kept on the tooth during penetration in the second embodiment. However, the pulp chamber locator could be kept on the tooth during the entire procedure, or it could be removed from the tooth during penetration, in either embodiment. If the pulp chamber locator is to be kept on the tooth, the hole in the plate should be made large enough to accommodate the burr or drill. If the pulp chamber locator is removed before penetration in the second embodiment, the dentist must somehow remember the indicated angle, because the indicator would not be present during penetration.

The invention can be modified in various ways. The number of struts can be varied. The plate portion and struts can be integrally formed, or formed separately and suitably joined. The structure of the plate and struts can be varied in other ways, as long as the device provides a hole substantially at, or in the vicinity of, the center.

In another modification, the marking tool could be omitted, provided that the dentist can otherwise remember the location of the hole of the pulp chamber locator, relative to the surface of the tooth.

These and other modifications, which will be apparent to the reader skilled in the art, should be considered within the spirit and scope of the following claims.

What is claimed is:

1. A method of locating a pulp chamber of a tooth, the method comprising:

a) fitting a pulp chamber locator over a crown of a tooth, the pulp chamber locator having a plate with a hole in a vicinity of a center of the plate, the plate defining an axis which is perpendicular to the plate, the pulp chamber locator having flexible and resilient struts attached to the plate, each strut having a first end which is attached to the plate and which is substantially perpendicular to the plate, and a second end which is free, wherein each strut is curved such that the free second end of each strut is curved towards the axis of the plate, the struts comprising resilient means for gripping the tooth, b) applying a marking tool to the hole so as to mark a spot on the tooth, and c) drilling into the tooth, starting at said spot, so as to form a channel leading to a pulp chamber of the tooth, wherein step (a) comprises inserting the pulp chamber locator over the tooth such that the second end of each strut engages the tooth in a vicinity of a cemento-enamel junction of the tooth.

2. The method of claim 1, wherein step (c) is preceded by the step of removing the pulp chamber locator from the tooth.

3. The method of claim 1, wherein the pulp chamber locator includes an indicator which is rotatably mounted on the plate, and wherein step (c) is preceded by the step of adjusting the indicator to show a correct entry angle into the tooth.

4. The method of claim 1, wherein the pulp chamber locator includes an indicator which is rotatably mounted on the plate, and wherein step (c) is preceded by the steps of adjusting the indicator to show a correct entry angle into the tooth, noting the correct entry angle, and then removing the pulp chamber locator from the tooth.

* * * * *